United States Patent [19]

Lau et al.

[11] Patent Number: 4,916,038

[45] Date of Patent: Apr. 10, 1990

[54] SUBSTITUTED AROMATIC SILANE COMPOUNDS AND METHOD FOR PREPARATION OF SAME

[75] Inventors: Kreisler S. Y. Lau, Alhambra; Susan L. Oldham, Torrance; William E. Elias, Redondo Beach; Stephen J. Bigus, Long Beach, all of Calif.

[73] Assignee: Hughes Aircraft Company, Los Angeles, Calif.

[21] Appl. No.: 237,816

[22] Filed: Aug. 29, 1988

Related U.S. Application Data

[62] Division of Ser. No. 46,013, May 7, 1987, Pat. No. 4,861,901.

[51] Int. Cl.$^4$ ............................................. B32B 9/04
[52] U.S. Cl. ..................................... 428/447; 528/32; 528/35; 528/43; 526/279; 427/387
[58] Field of Search ................ 528/35, 32, 43; 526/279; 427/387; 428/447

[56] References Cited

U.S. PATENT DOCUMENTS

| | | | |
|---|---|---|---|
| 4,233,427 | 11/1980 | Bargain et al. | 528/35 |
| 4,587,169 | 5/1986 | Kistner | 428/447 |
| 4,766,189 | 8/1988 | Tsuetaki | 526/279 |

Primary Examiner—Melvin I. Marquis
Attorney, Agent, or Firm—Mary E. Lachman; W. K. Denson-Low

[57] ABSTRACT

A new group of silane compounds in which silicon atoms are linked together by a hydrocarbon chain and which comprise phenyl groups substituted with an epoxy group or an ethenyl group. The compounds of the present invention have the formula

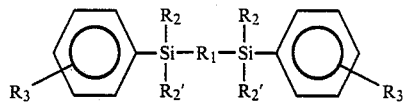

where $R_1$ is selected from the group consisting of:
(a) an aliphatic hydrocarbon group containing 2 to 10 carbon atoms, and
(b) a group having the formula

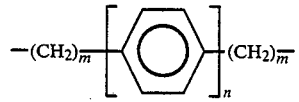

where
$n = 1$ to 3
$m = 0$ to 5;

$R_2$ and $R_2'$ are each selected from the group consisting of an alkyl group containing 1 to 4 carbon atoms, an unsubstituted aryl group, and a substituted aryl group; and $R_3$ is selected from the group consisting of:

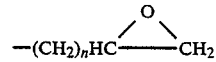

and

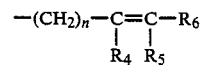

where $R_4$, $R_5$, and $R_6$ ae each selected from the group consisting of H, an alkyl group containing 1 to 4 carbon atoms, and an aryl group; and $n = 0$ to 10.

10 Claims, No Drawings

SUBSTITUTED AROMATIC SILANE COMPOUNDS AND METHOD FOR PREPARATION OF SAME

This is a division of application Ser. No. 07/046,013, filed May 5, 1987, now U.S. Pat. No. 4,861,901.

BACKGROUND OF THE INVENTION

1. Field of the Invention

The present invention relates generally to silicon-containing substituted aromatic compounds. More particularly, the present invention relates to compounds comprising silicon atoms linked together by a hydrocarbon chain and further comprising phenyl groups substituted with a glycidyl group or an allylic group.

2. Description of the Background Art

Epoxy resins are widely used as adhesives, encapsulants, and coatings for a variety of applications. In particular, for application to structural and electronic devices, epoxy resins are useful since they provide mechanical protection, good substrate adhesion, thermal and oxidative stability, and moisture and solvent resistance. In addition, compliance is a highly desirable property for these resins since it allows the dissipation of stress that accompanies thermal and mechanical cycling of the encapsulant. Furthermore, enhanced toughness provides mechanical protection against fracture damage. However, state-of-the-art systems exhibiting such compliance generally possess poor thermal stabilities. Another important property is the repairability of the adhesive, coating, or encapsulant. As expected, a rigid system is generally more difficult to repair and replace than a ductile one.

One group of epoxy resins particularly useful for electronic applications consists of epoxysilicone compounds, which are compounds comprising silicon atoms joined together by oxygen linkages and further comprising terminal glycidyl groups. Such epoxysilicone compounds have been known for many years and are described, for example, in the publications by Bilow, Lawrence and Patterson, "Synthesis and Polymerization of 1,3-bis(2,3-epoxypropylphenyl)tetramethylsiloxanes and Related Compounds, *Journal of Polymer Science*, Volume 5, 1967, pages 2595 to 2615 and by Patterson and Bilow, "Polymers from Siloxane-Containing Epoxides," *Journal of Polymer Science*, Volume 7, 1969, pages 1099 to 1110. As described in these references, such epoxysiloxane compounds were prepared by reacting the Grignard reagent derivable from an allybromobenzene with a large excess of dichlorodimethylsilane. The resulting compound, chlorodimethyl(allyphenyl)silane, must be isolated from excess dichlorodimethylsilane by repeated distillation steps. Chlorodimethyl(allylphenyl)silane was then hydrolyzed to give 1,3-bis(allyphenyl)-1,1,3,3-tetramethyl-1,3-disiloxane. Epoxidation was effected either with 3-chloroperoxybenzoic acid or trifluoroperoxyacetic acid. However, such a procedure is not only tedious, but also yields a product contaminated by impurities produced by rearrangement or reversion in which —Si—O— groups break away from the rest of the molecule and form macrocycles or higher linear chains. In addition, the corrosive trifluoroperoxyacetic acid was difficult and dangerous to prepare on a large scale, and the 3-chlorobenzoic acid side product generated in the epoxidation reaction was so soluble in the desired product that complete removal of this acid residue was impossible. Furthermore, such a process is not conducive to tailor making the length of the siloxane chain.

When epoxy resins are used in structural applications for outer space, such as for adhesives or coatings in satellite components, the resin must not only be able to withstand the temperature extremes encountered in space, for example −148° F. (−100° C.) to 212° F. (100° C.), for extended periods of time, such as several years, but also be able to withstand the higher temperatures (350° F. or 177° C.) encountered in rigorous space applications for shorter periods of time. In addition, the material must meet the National Aeronautics and Space Administration (NASA) outgassing requirements, i.e., < 1% total mass loss, and ≦ 0.10% collectible volatile condensable materials, to insure that the material does not release gaseous component substances which would undesirably accumulate on other spacecraft parts in the outer-space vacuum. Heretofor, ductile, processible epoxy resins meeting all these requirements have been unobtainable.

Thus, a need exists for an epoxy resin for electronic and structural space applications which is tough, thermally and oxidatively stable, repairable, resistant to moisture and solvents, and which possesses low outgassing characteristics. In addition, a need exists for the preparation of the ψ, ω-alkenyl compounds from which such epoxy resins, among others, may be formed. The next to the lowest homolog of the ψ, ω-alkenyl group is the allyl group from which the glycidyl group is derived.

SUMMARY OF THE INVENTION

The general purpose of the present invention is to provide new and improved silicon-containing substituted aromatic compounds. These compounds possess most, if not all, of the advantages of the above prior art compounds while overcoming their above-mentioned significant disadvantages.

The above-described general purpose of the present invention is accomplished by providing a new group of silane compounds in which silicon atoms are linked together by a hydrocarbon chain and which comprise phenyl groups substituted with a glycidyl-terminated alkyl group or a ψ,ω-alkenyl group. The compounds of the present invention have the formula

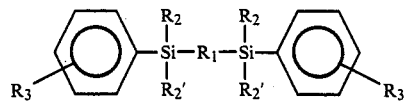

wherein:
$R_1$ is selected from the group consisting of:
(a) an aliphatic hydrocarbon group containing 2 to 10 carbon atoms, and
(b) a group having the formula

where
n=2 to 3
m=0 to 5;

$R_2$ and $R_{2'}$ are each selected from the group consisting of an alkyl group containing 1 to 4 carbon atoms, an unsubstituted aryl group, and a substituted aryl group; and $R_3$ is selected from the group consisting of:

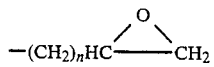

and

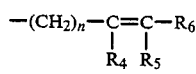

where $R_4$, $R_5$, and $R_6$ are each selected from the group consisting of H, an alkyl group containing 1 to 4 carbon atoms, and an aryl group; and n = 0 to 10.

Accordingly, it is a purpose of the present invention to provide epoxy resins for use as adhesives, encapsulants, or coatings, which are tough, compliant, thermally and thermo-oxidatively stable, and resistant to moisture and solvents.

Another purpose of the present invention is to provide epoxy resins of the type described which further possess low outgassing characteristics and are suitable for space applications.

A further purpose of the present invention is to provide a process for forming the above-described epoxy resins in high purity.

Still another purpose of the present invention is to provide the monomers from which the above-described epoxy resins may be prepared.

Another purpose of the present invention is to provide a process for forming the above-described epoxy monomers in high purity.

Yet another purpose of the present invention is to provide silicon-coating difunctional $\psi,\omega$alkenyl monomers for use in forming polymers which are tough, compliant, thermally and thermo-oxidatively stable, and resistant to moisture and solvents.

Another purpose of the present invention is to provide a process for forming the above-described difunctional $\psi,\omega$-alkenyl monomers in high purity.

Still another purpose of the present invention is to provide polymers of each of the above-described monomers.

Another purpose of the present invention is to provide copolymers of each of the above-described monomers in which the flexibility and dimensional stability of the copolymer can be controlled and predetermined.

A further purpose of the present invention is to provide a coating which is resistant to abrasion by mechanical means or by plasma.

The foregoing and other objects, features, and advantages of the present invention will be apparent from the following more particular description of the preferred embodiments of the invention.

DETAILED DESCRIPTION OF THE INVENTION

Compounds in accordance with the present invention have the general formula:

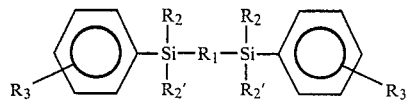

where $R_1$ is selected from the group consisting of:
 (a) an aliphatic hydrocarbon group containing 2 to 10 carbon atoms, and
 (b) a group having the formula

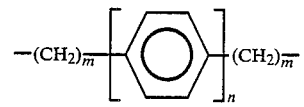

where n = 1 to 3 m = 0 to 5;

$R_2$ and $R_2'$ are each selected from the group consisting of an alkyl group containing 1 to 4 carbon atoms, an unsubstituted aryl group, and a substituted aryl group; and $R_3$ is selected from the group consisting of:

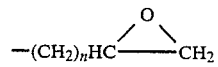

and

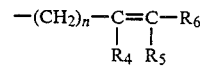

where $R_4$, $R_5$, and $R_6$ are each selected from the group consisting of H, an alkyl group containing 1 to 4 carbon atoms, and an aryl group; and n = 0 to 10.

The groups $R_2$ and $R_2'$ may each be a $C_1$ to $C_4$ alkyl group or a substituted or unsubstituted aryl group, such as phenyl, naphthyl, anthryl, or phenanthryl. It is anticipated that the fused aromatic groups would impart unique photochemical properties to the compound in which they are incorporated. The phenyl group may be substituted with, for example, a methyl, carboxyl, or halogen group, and the substitution may be in the meta or para position with respect to the silicon attachment.

The group $R_3$ may be a glycidyl-terminated alkyl group, in which case the monomer is useful for forming epoxy resins as previously discussed. The compound of the present invention in which $R_3$ is a glycidyl-terminated alkyl group is referred to herein as the "epoxy monomer." Alternatively, $R_3$ may be a $\psi,\omega$-alkenyl group, in which case the monomer is useful for forming polymers and copolymers for application as low dielectric materials. The compound of the present invention in which $R_3$ is a $\psi,\omega$-alkenyl group is referred to herein as the "ethenyl monomer".

A preferred compound in accordance with the present invention is 2,5-bis(3-glycidylphenyl)-2,5-dimethyl-2,5-disilahexane where, in the above formula, $R_1$ is $—CH_2—CH_2—$, $R_2$ and $R_2'$ are each $—CH_3$, and $R_3$ is a glycidyl-terminated methyl group attached to the benzene ring at the position meta or para to the silicon attachment. Other preferred compounds include homologs of the above-noted compound in which $R_1$ is a $C_3$ to $C_{10}$ aliphatic hydrocarbon group, most preferably $(-CH_2-CH_2-)_3$ and $(-CH_2-CH_2-)_4$. Additional preferred compounds include those having the above-noted formula in which $R_1$ is a $C_2$ to $C_{10}$ aliphatic hydrocarbon group, $R_2$ is $-CH_3$, $R_2'$ is $-C_6H_5$, and $R_3$ is a glycidyl-terminated alkyl group. Thermal stability is enhanced in still other preferred compounds in which a phenylene group is incorporated in the straight chain between the silicon atoms, i.e., $R_1$, or in which one of the two methyl groups on each silicon atom, i.e. $R_2$ or $R_2'$, is replaced by a phenyl group. Such preferred compounds have the formula noted above with $R_3$ being a glycidyl-terminated alkyl group and in which $R_1$ is $-CH_2-C_6H_4-CH_2-$, and $R_2$ and $R_2'$ are each $-CH_3$, or in which $R_1$ is $-CH_2-C_6H_4-CH_2-$, $R_2$ is $-CH_3$, and $R_2'$ is $-C_6H_5$. Compounds corresponding to those noted above except having a $\psi,\omega$-alkenyl group, such as an allyl group, as $R_3$ are also preferred compounds in accordance with the present invention.

Exemplary preparation of 2,5-bis(3-glycidylphenyl)-2,5-dimethyl-2,5-disilahexane and its allyl precursor is described in Example 1 herein. The homologs thereof are prepared in a similar manner by substituting the appropriate $\beta,\psi$-dichloro-$\beta,\psi$-disilaliphatic reactant

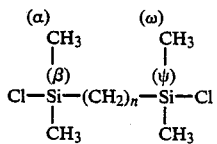

where n=an integer in the Grignard synthesis step as described in Examples 6–7 and 10–12 herein. Thus, by appropriate choice of the above-noted dichlorodisilaliphatic reactant, the internal chain length of the silane compounds of the present invention can be pre-defined, which represents a significant advancement over the previously discussed prior art processes. The $\beta,\psi$-dichloro-$\beta,\psi$-disilaliphatic compounds of interest are either commercially available or can be formed by known synthesis methods, such as referenced by T. L. Guggenheim, *Tetrahedron Letters*, volume 25, pages 1233–1254, 1984. As indicated in Example 4, the para isomer of the compound described in Example 1 is obtained by substituted 3-(4-bromophenyl)-propene for 3-(3-bromophenyl)propene in the reaction described in Example 1. The para isomer will lead to epoxy resins and polymers derived from the ethenyl monomer that exhibit greater dimensional stability, i.e., higher glass transition temperatures, than those derived from the meta isomers, while retaining acceptable toughness characteristics.

The compound 2,5-bis(3-glycidylphenyl)-2,5-dimethyl-2,5-disilahexane is prepared by reacting the Grignard reagent derived from 3-(3-bromophenyl)propene and magnesium with 2,5-dichloro-2,5-dimethyldisilahexane in anhydrous tetrahydrofuran to form 2,5-bis(3-allylphenyl)-2,5-dimethyl-2,5-disilahexane. The latter is then allowed to undergo epoxidation with 3-chloroperoxybenzoic acid (MCPBA) to form 2,5-bis(3-glycidylphenyl)-2,5-dimethyl-2,5-disilahexane. It has been found advantageous to use 3-chloroperoxybenzoic acid in the above-noted epoxidation reaction since this compound is an inexpensive and efficient epoxidation reagent and, further, since the side product, meta-chlorobenzoic acid, is not soluble in the epoxysilane product and therefore can be virtually completely removed. Such is not the case in the previous state-of-the-art syntheses of epoxysiloxanes, where the chlorobenzoic acid side product is soluble in the epoxy-silicone resin. This solubility of the benzoic acid side product makes isolation of the desired epoxy-silicone product difficult and tedious. Thus, the present invention avoids this prior art problem. Another preferred oxidizing agent according to the present invention is trichloroperoxyimidic acid (TCPIA) generated in situ by the reaction of trichloroacetonitrile and 30–50 percent hydrogen peroxide is a biphasic medium, such as water and dichloromethane.

The epoxy monomer compounds formed in accordance with the present invention may be cured with known curing agents such as 1,3-bis(3-aminopropyl)-1,1,3,3-tetramethyl-1,3-disiloxane (known as APMD), 1,3-bis-(3-aminobutyl)-1,1,3,3,-tetramethyl-1,3-disiloxane (known as ABMD), triethylenetetraamine, meta-phenylenediamine, 4,4'-methylenedianiline, diaminodiphenylsulfone, nadic methylanhydride, methyltetrahydrophthalic anhydride, methylhexahydrophthalic anhydride, and 2-ethyl-4-methylimidazole, or other amine, amide, acid, and nitrogen-containing curing agents to form a resin. The term "resin" is used herein to mean a mixture of polymerizable materials either before or after polymerization.

The epoxy monomer compounds of the present invention may be polymerized with the above-noted epoxy curing agents to form homopolymers. These polymers have been found to be very effective as abrasion-resistant coatings, as discussed in Example 17. Alternatively, the present epoxy monomer may be copolymerized with other monomers to form the corresponding copolymers. In particular, the epoxy monomer of the present invention may be copolymerized with commercially available epoxy materials, such as DGEBA (the diglycidyl ether of Bisphenol A, available from Shell Chemical), of which EPON 825 is an industry standard, epoxy phenol novalacs (such as DEN 438, available from Dow Chemical), epoxy cresol novalacs (such as ECN 1235, available-from Ciba Geigy) and tetraglycidylmethylene dianilines (such as MY 720, available from Ciba Geigy), to improve the compliance of such materials. (The term "compliance" is used herein to mean the ability of an object to yield elastically when a force is applied; flexibility).

In addition, the epoxy monomers of the present invention may be copolymerized with known silicone materials, such as poly(dimethylsiloxanes), poly-(methylphenylsiloxanes), and poly(diphenylsiloxanes), to provide crosslinking and network formation which provide dimensional stability. These commercial silicone materials may be obtained from Dow-Corning, Petrarch, and Silar, among others.

Thus, depending on the relative proportions of the epoxy monomer of the present invention and the material with which it is copolymerized (epoxy or silicone), a material of controlled and predetermined rigidity may be formed. The epoxy compounds of the present invention are used in the amount of 10 to 80 percent by weight of the mixture, preferably 30 to 50 percent. The meta isomers of the epoxy monomers of the present invention have been found effective for increasing the flexibility of known epoxy materials as described in Example 14. The para isomers of the epoxy monomers of the present invention have been found effective for increasing the toughness of known epoxy materials as described in Example 15. ("Toughness" is used herein to mean the ability of a material to absorb energy by plastic deformation; being intermediate between soft and brittle.) Suitable curing agents for such copolymerization include: amino-functional siloxanes such as 1,3-bis-(3-aminopropyl)-1,1,3,3-tetramethyl-1,3-disiloxane and 1,3-bis-(3-aminobutyl)-1,1,3,3-tetramethyl-1,3-disiloxane; aliphatic amines, such as triethylenetetraamine, diethylenetriamine and methanediamine; aromatic amines such as meta-phenylenediamine, 4,4'-methylenedianiline, and diaminodiphenylsulfone; polyanhydrides such as nadic methylanhydride, methyltetrahydrophthalic anhydride, methylhexahydrophthalic anhydride; and other standard epoxy curing agents.

The ethenyl monomer compounds formed in accordance with the present invention may be polymerized using known olefin polymerization techniques such as described in S. R. Sandler and W. Karo, "Polymer Syntheses", Volume III, Chapter 8, Academic Press, 1980 and H. G. Elias, "Macromolecules, Volume 2. Synthesis and Materials", Chapter 25, Plenum Press, New York, 1977. Such polymers have improved flexibility, thermal and thermo-oxidative stability and resistance to moisture and solvents, when compared to corresponding non-silicon-containing hydrocarbon compounds. In addition, the ethenyl monomer compounds of the present invention may be copolymerized with other materials, such as N-(vinylphenyl)phthalimide using known methods, such as described by Sandler and Karo referenced above. Depending on the relative proportions of the ethenyl monomer and the material with which it is copolymerized, a material of controlled and predetermined rigidity may be formed. The ethenyl compounds of the present invention are used in the amount of 10 to 90 percent by weight of the mixture, preferably 30 to 70 percent.

Examples of practice of the present invention are as follows.

EXAMPLE 1

This example illustrates the preparation of 2,5-bis(3-allylphenyl)-2,5-dimethyl-2,5-disilahexane and 2,5-bis(3-glycidylphenyl)-2,5-dimethyl-2,5-disilahexane in accordance with the present invention.

A. Preparation of 3-(3-bromophenyl)propene:

In accordance with accepted laboratory practice, the glassware used for the Grignard reaction described below was flame-dried and purged with dry nitrogen. A small portion of a solution of 118 g (0.50 moles) of 1,3-dibromobenzene in 50 ml of anhydrous ether was added to 14.132 g (0.58 g-atom) of magnesium turnings in 150 ml of anhydrous ether. The reaction started almost immediately to form the Grignard reagent. (In situations where reaction does not proceed immediately, a few drops of ethyl iodide may be added to induce a reaction.) After a steady reflux was established, the rest of the dibromobenzene solution was added dropwise to maintain the reflux. The total addition required 45 minutes. The final mixture was heated for an additional hour. A solution of 46 ml of allyl bromide (65 g, 0.537 moles) in 50 ml of anhydrous ether was added dropwise. The final mixture was heated for an additional hour.

The mixture was poured into 1 liter of saturated aqueous ammonium chloride solution, and the organic phase was separated. The aqueous phase was extracted with two 100-ml portions of ether. The ethereal portions were combined, washed with 100 ml of water and dried over anhydrous magnesium sulfate. The concentrated filtrate was finally distilled (60°–62° C./0.5 torr or 48°–50° C./0.1 torr) to yield 81.84 g (0.416 moles, 83.2%) of a clear liquid. Nuclear magnetic resonance (NMR) spectrometry showed a diagnostic splitting pattern of an allylic side group and a characteristic (complex) meta-ring substitution, unequivocally establishing the identity of this product as the expected 3-(3-bromophenyl)propene.

$^1$H NMR(CDCl$_3$) 3.16, 3.28 (bd, 2H, benzylic H's), 4.82–5.22 (2 m, 2H, terminal H's on olefinic bond), 5.55–6.60 (broad complex multiplet, 1H, olefinic H), and 6.92–7.60 ppm (2 m, 4H, aromatic).

B. Preparation of 2,5-bis(3allylphenyl)-2,5-dimethyl-2,5-disilahexane:

The compound 2,5bis(3-allylphenyl)-2,5 dimethyl-2,5-disilahexene (Compound 3 below where n=1) was prepared in accordance with the following reaction.

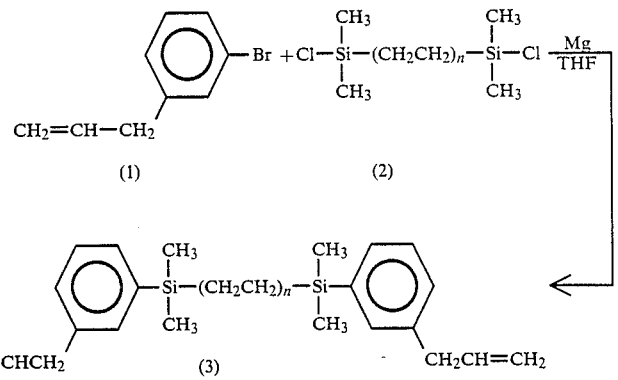

Into a flame dried reaction vessel under nitrogen were placed 10.45 g of magnesium (from Fluka Chemicals) and 150 ml of anhydrous tetrahydrofuran (THF) which was freshly distilled from sodium. An aliquot of a solution of 85.5 g (containing 0.3875 moles of assay) of 3-(3-bromophenyl)propene, Compound 1 above, prepared as described in Step A above, in 200 ml of anhydrous THF was added from the addition funnel. The reaction started almost instantly. After the mixture reached reflux, the addition was continued until all the reactant was added (1 hr). The mixture was heated at reflux for 1 more hour and treated with a solution of 39.55 g (0.184 mole) of 2,5-dichloro-2,5-dimethyl-2,5-disilahexane, Compound 2, n=1 above, from Petrarch Chemicals, in 100 ml of anhydrous THF, added during reflux over 0.5 hr. The reaction mixture obtained was heated further for another 1.5 hr, cooled and stirred for 18 hours under nitrogen.

The mixture was poured into 1.5 liters of aqueous ammonium chloride and extracted with three 50-ml portions of diethylether. All organic fractions were combined, washed with water and dried over anhydrous magnesium sulfate. After filtering and concentrating, the resulting oil was distilled. The low boiling fractions collected (up to an oil bath temperature of 150° C.) were shown to contain mono- and diallylbenzenes. The pot residue oil, which did not discolor, was shown to be the desired product, Compound 3, where $n=1$ above, by its NMR absorptions showing perfect ratios of peak area integrations.

A second batch of Compound 3, where $n=1$ was prepared by the exact procedure described above except that the dichlorosilane reactant, Compound 2, where $n=1$, was purified by distillation (at bp 198° C/734 torr) before use. The distilled product, Compound 2, $n=1$, had a melting point of 37° C.

Purification of the water white product oil of each batch was effected by distillation under reduced pressure: bp 155° C./$10^{-4}$ torr. (The external heating oil bath reached a temperature of 220° C. but did not cause appreciable darkening of the product being distilled). At the end of the distillation, the pot residue was orange-brown and appeared to be more viscous than before distillation. The NMR results for the product of the first batch were as follows: $^1$H NMR (CDCl$_3$): δ 0.25 (s, 12H, SiCH$_3$), 0.57 (s, 4H, C$\underline{H}_2$ Si(CH$_3$)$_3$), 3.32, 3.43 (2 bs, 4H, 2 methylenes), 4.97, 5.17 (2 bm, 4H terminal H's of olefin), 5.67–6.38 (m, 2H, vinyl proton), and 7.30 ppm (bm, 8H, aromatics).

The $^1$H NMR results for the product of the second batch were the same as those for the first batch. In addition, the following NMR results were obtained for the product of the second batch.

$^1$H NMR (250 MHz, CDCl$_3$): δ 0.29 (s, 12H), 0.73 (s, 4H), 3.40 (d, 4H, J=6.6 Hz), 5.07 (bs, 2H), 5.12 (d, 2H, J=7.8 Hz), 5.95–6.05 (Complex m, 2H), and 7.17–7.38 ppm (Complex m, 8H).

$^{13}$C NMR (62.8 MHz, CDCl$_3$): δ −3.2, 8.1, 40.6, 116.3, 128.1, 129.4, 131.7, 134.1, 137.8, 139.4 and 139.7 ppm (11 lines as expected).

Characterization of the purified product also included mass spectrometry, infrared spectroscopy, elemental analysis and refractive index measurements.

Refractive index measured at 24° C.: 1.5361.

IR (Neat): 2960, 2910 (m,sh), 1640 (m,sh), 1410 (m,br), 1250 (s,sh), 1132, 1120 (m,sh), 1052 (m,sh), 994 (m,sh), 912 (s,br), 862, 830, 810, 775 cm-1(s,br). [m=medium, s=strong, sh=sharp, br=broad].

Mass Spectrum (22.0 V); m/e 378 (M+, 31.8) 363 (50.0), 309 (30.2), 277 (24.1), 260 (18.3), 188 (28.8), 176 (53.1), 175 (100.0), 160 (29.2), 135 (14.8), 113 (7.8), and 86 (16.7).

High resolution mass spectrometry gave a molecular ion exact mass measurement of 378.2187 (theoretical: 378,2191).

Analysis. Calculated for C$_{24}$H$_{34}$Si$_2$ (378,708): C, 76.12; H, 9.05; Si, 14.83. Found: C, 75.26; H, 9.10; Si, 15.64.

Preparation of 2,5-bis(3-glycidylphenyl)-2,5-dimethyl-2,5-disilahexane:

The compound 2,5-bis(3-glycidylphenyl)-2,5-dimethyl-2,5-disilahexane, Compound (4) below where $n=1$, was prepared in accordance with the following reaction.

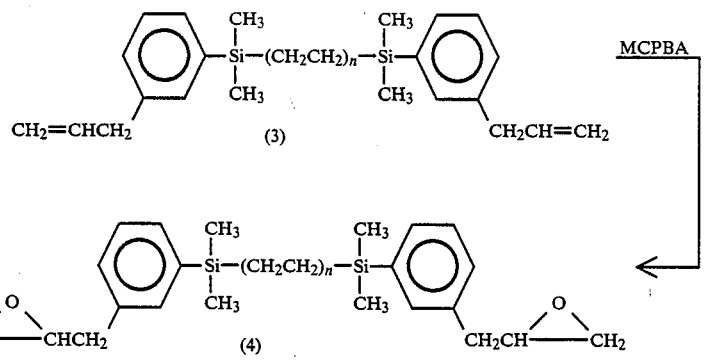

where $n=1$, was purified by distillation (at bp 198° C/734 torr) before use.

To a solution of 34.15 g (80% purity, 27.84 g assay, 0.161 mole) of 3-chloroperoxybenzoic acid (MCPBA) in 400 ml of dichloromethane was added a solution of 28.50 g (0.0754 mole) of 2,5-bis(3-allylphenyl)-2,5-dimethyl-2.5-disilahexane, Compound (3), where $n=1$, prepared as described in Step B above, in 50 ml of dichloromethane. The clear solution was heated for 0.5 hr at reflux. The onset of reaction was marked by the clear solution turning turbid. Precipitation of a white solid ensued. The resulting sludge was stirred for 18 hr, heated for 1 hr and cooled.

The sludge was diluted with an equal volume of hexane and filtered to remove 3-chlorobenzoic acid residues. (Alternatively, the sludge was concentrated and the residue was triturated with hexane.) The hexane filtrate was extracted with four 125-ml portions of a 0.4M sodium hydroxide solution. From the alkaline washings after acidification and extraction with dichloromethane, there was recovered a small batch of 3-chlorobenzoic acid residues. The total recovered 3-chlorobenzoic acid residue was 31.6 g, representing a 96.9% material balance.

The organic phase after the washings was dried over magnesium sulfate, filtered, and concentrated to an oil. Further heating at 60° C/1.0 torr for 4 hr removed volatiles and produced a tan-colored oil. Purification by distillation was attempted and was found to be difficult. Furthermore, using gel permeation chromatography, the distillate was found to contain dimeric products.

The product was shown to be Compound 4 where $n=1$, by its NMR spectrum which revealed perfect integration ratios of the absorptions. As indicated below, the measured epoxy equivalent of the product was very close to the theoretical value.

$^1$H NMR (CDCl$_3$) ⊕ 0.23 (s, 12H, SiCH$_3$), 0.65 (s, 4H, CH$_2$Si(CH$_3$)$_3$), 2.46–3.30 (3closely spaced m's, 10H, characteristic of H's on epoxide), and 7.33 ppm (bs, 8H, aromatics).

Epoxy equivalent weight:
Measured: 230 gm/(gm mole epoxy)
Theoretical: 205 gm/(gm mole epoxy)

Epoxidation of the second batch of Compound 3, n=1 as described in Step B above was performed as described immediately above. The product Compound 4, n=1 had an NMR spectrum which was superimposible on that of the first batch of Compound 4, n=1. Additional characterization is described below.

$^1$H NMR (250 MHz, CDCl$_3$): δ 0.28 (s, 12H), 0.68 (s, 4H), 2.56, 2.57, 2.58, 2.59 (dxd, 2H), 2.78–3.00 (m, 6H), 3.17 (bm, 2H), and 7.26–7.46 ppm (complex m, 8H).

$^{13}$C NMR (62.8 MHz, CDCl$_3$): δ −3.4, 8.0, 39.0, 47.0, 52.6, 128.0, 129.6, 132.1, 134.4, 136.5, and 139.8 ppm.

Mass Spectrum (22.0 V): m/e 410(24), 394(16), 367(20), 337(22), 311(17), 161(29), 117(100), 75(83).

High resolution mass spectrometry gave a molecular ion exact mass measurement of 410.2077 (theoretical: 410.2089).

EXAMPLE 2

This example illustrates the preparation and characterization of cured resins from the 2,5-bis-(3-glycidylphenyl)-2,5-dimethyl-2,5-disilahexane, Compound (4), n=1, prepared as described in Example 1.

The Compound 4 where n=1 prepared as in Example 1 was cured with 1,3-bis(3-aminopropyl)-1,1,3,3-tetramethyl-1,3-disiloxane (APMD) at 90% stoichiometry. The cure schedule was 14 hours at 66° C. and 2 hours at 121° C.

Differential scanning calorimetry (DSC) of the cured resin revealed a glass transition temperature (Tg) of 16° C. with a decomposition temperature (Td) of 260° C. It is noteworthy that this compound has a relatively low Tg and relatively high Td as compared to commercial epoxy materials. Further characterization by thermomechanical analysis (TMA) showed a softening temperature around 5° C. Rheometric dynamic mechanical spectroscopy (RDMS) analysis gave a Tg of 32° C., and a dynamic storage modulus (G') value of 1.7×10$^7$ dynes/cm$^2$ (247 psi) for a thermally conditioned specimen.

The outgassing results showed a total mass loss (TML) of 2.06% and collectible volatile condensable material (CVCM) of 0.61%. The outgassed material was found to be unreacted epoxy. These results indicated that by using the appropriate stoichiometry (i.e., reacting all the epoxy), the outgassing can be brought within NASA requirements. (See Table II, fifth item). The relatively low outgassing properties of this resin are probably due to the stability of the two-carbon chain between the silicon atoms. The stable methylene chain does not have the propensity to undergo rearrangement-reversion as the prior art siloxane chain does. Therefore, no undesirable oligomers were found when Compound 4 where n=1 was cured. Hydrolytically, the disilethylene chain is expected to be more stable than the siloxane chain.

Additional batches of the above-noted resin were prepared by curing Compound 4 where n=1 with various amounts of the 1,3-bis(3-aminopropyl)-1,1,3,3-tetramethyl-1,3-disiloxane (APMD) curing agent to obtain 90%, 95%, 100%, and 107% stoichiometry, amine to epoxy. The ambient temperature viscosity of the uncured resin was 470 centipoise, as determined using a Brookfield viscometer. The cure schedule was 14 hours at 66° C. and 3 hours at 121°C. The cured resins were clear and ranged from light tan to light brown in color. The physical properties ranged from a hard rubber (90% stoichiometry) to a stiff but tough plastic (107% stoichiometry). The differential scanning calorimetry results are summarized in Table I and indicate Tg values from 10° C. (for the 90% stoichiometry) to 37° C. (for the 110% stoichiometry) and decomposition temperatures (Td's) from 240° C. (for the 95% stoichiometry) to 340° C. (for the 107% stoichiometry). The high decomposition temperature of the latter specimen was noteworthy. Commonly used toughened epoxy resins possess much lower decomposition temperatures (significantly below 300° C.). The low decomposition temperatures of commercially available compliant epoxies are generally due to the poor thermal resistance of the commonly employed flexibilizing agents such as polysulfides, digylcidyl esters of linoleic acid dimer, carboxy-terminated butadiene acrylonitrile (CTBN) rubbers, aliphatic polyamides, and amido-polyamides.

Adhesive peel strength testing was carried out with the 90% stoichiometry formulation with a 5 mil bondline. The measured peel strength of 19 lbs per inch width (piw) indicated that the material has a high level of toughness. As a comparison, typical peel strength for a brittle material is ≦ 2 piw, and a compliant (rubbery) material will have typical peel strengths between 10 and 25 piw.

TABLE I
DSC RESULTS FOR EXAMPLE 2

| Run No. | Epoxy Equivalent Weight | | Stoichiometry (%) | Tg (°C.) | Td (°C.) |
|---|---|---|---|---|---|
| | Actual | Theoretical | | | |
| 1 | 230 | 205 | 90 | 10 | 280 |
| | | | 95 | 17 | 240 |
| | | | 100 | 21 | 290 |
| | | | 107 | 25 | 340 |
| | | | 107[a] | 33 | 335 |
| 2 | 272 | 205 | 107[a] | 28–44 | 335 |
| 3 | 229 | 205 | 110[a] | 25–37 | 335 |

[a]Molecularly distilled at 124° C. Run Nos. 1 and 2, monomer prepared by method of Example 1, first batch. Run No. 3, monomer prepared by method of Example 1, second batch.

Outgassing experiments performed on the various formulations are summarized in Table II. The molecularly distilled 107% stoichiometry sample yielded a total mass loss (TML) of 0.64% and a collectible volatile condensable material (CVCM) weight of 0.03%. When tested in accordance with the American Society for Testing Materials (ASTM) specification, the NASA requirement for passing outgassing tests for space applications is TML ≦ 1.0% and CVCM ≦ 0.10%.

The epoxy resin prepared in accordance with Example 1 and having an epoxy equivalent weight of 272 had a viscosity of 410–420 centipoise and a refractive index of 1.5458 (measured at 24° C.)

TABLE II
STOICHIOMETRY STUDY - OUTGASSING DATA FOR EXAMPLE 2

| Run No. | Epoxy Equivalent Weight Actual | Theoretical | Stoichiometry (%) | TML[a] | CVCM[b] | WVR[c] |
|---|---|---|---|---|---|---|
| 1[e] | 230 | 205 | 90 | 3.24 | 0.56 | 0.1 |
| | | | 95 | 2.67 | 0.20 | 0.09 |
| | | | 100 | 2.22 | 0.05 | 0.09 |
| | | | 107 | 2.16 | 0.03 | 0.08 |
| | | | 107[d] | 0.64 | 0.03 | 0.09 |
| 2 | 272 | 205 | 107[d] | 1.58 | 0.13 | 0.08 |

[a] Total mass loss
[b] Collectible volatile condensable materials
[c] Water vapor recovery
[d] Sample was molecularly distilled at 124° C.
[e] Run Nos. 1 and 2, monomer prepared by method of Example 1, first batch.

EXAMPLE 3

This example illustrates the preparation of 2,5-bis(4-allylphenyl)-2,5-dimethyl-2,5-disilahexane and 2,5-bis(4-glycidylphenyl)-2,5-dimethyl-2,5-disilahexane. The procedure described in Example 1 was followed with the exceptions noted below.

A. Preparation of 3(4-bromophenyl) propene:

The procedure described in Example 1, Step A was followed except that 1,3-dibromobenzene was replaced by 1,4-dibromobenzene and the product was 3-(4-bromophenyl) propene having the following formula:

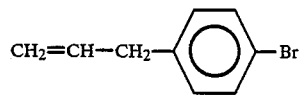

The NMR results for this product were as follows: NMR (CDCl$_3$) δ 3.30 (bd, 2H, benzylic H's) 4.92, 5.15 (2bm, 2H, geminal H's), 5.56–6.31 (m, 1H, vinyl H), and 7.20 ppm (q, 4H, J=8 Hz, aromatic).

B. Preparation of 2,5-bis(4-allylphenyl)-2,5-dimethyl-2,5-disilahexane:

The procedure described in Example 1, Step B was followed except that 3-(4- bromophenyl) propene was substituted for 3-(3-bromophenyl) propene. The product, obtained in 72% yield, was 2,5-bis(4-allylphenyl)-2,5-dimethyl-2,5-disilanexane having the following formula:

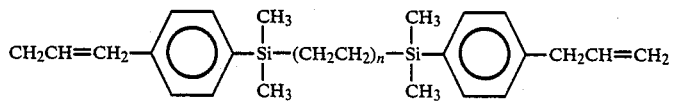

n = 1

The NMR results for this product were as follows: NMR (CDCl$_3$) δ 0.25 (s, 12H, SiCH$_3$), 0.57 (s, 4H, —CH$_2$, Si), 3.32, 3.43 (2 bs, 4H, —CH$_2$—), 4.97, 5.17 (2 bm, 4H, geminal) 5.67–6.38 (m,2H, vinyl), and 7.30 ppm (q,8H, J=7H, aromatic).

C. Preparation of 2,5-bis(4-glycidylphenyl)-2,5-dimethyl-2,5-disilahexane:

The procedure described in Example 1, Step C was followed except that 2,5-bis(4-allylphenyl)-2,5-dimethyl-2,5-disilahexane was substituted for 2,5-bis(3-allylphenyl)-2,5-dimethyl)-2,5-disilahexane. The product was 2,5-bis(4-glycidiphenyl)-2,5-dimethyl-2,5-disilahexane, Compound 5, having the formula:

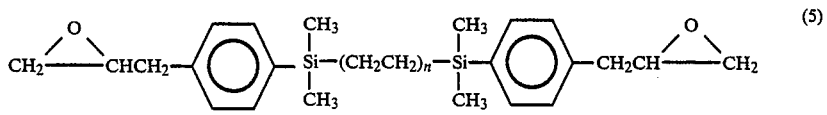

n = 1

After the solvents were stripped off, the crude Compound 5 was further purified by passing down a Kontes design falling film molecular distillation apparatus at 80° C. and at a pressure less than $1 \times 10^{-4}$ torr.

The NMR results for this product were as follows: NMR (CDCl$_3$) δ 0.23 (s, 12H, SiCH$_3$), 0.65 (s, 4H, CH$_2$—Si), 2.46–3.30 (3 m's, 10H, characteristic of H's on epoxide), and 7.30 ppm (distorted q, 8H, aromatic).

EXAMPLE 4

This example illustrates the preparation and characterization of a cured resin from the 2,5-bis-(4-glycidylphenyl)-2,5-dimethyl-2,5-disilahexane, Compound 5 where n=1, prepared as described in Example 3.

The Compound 5, n=1 prepared as in Example 3 was cured with 1,3-bis(aminopropyl)-1,1,3,3-tetramethyl-1,3-disiloxane (APMD) at 100% stoichiometry. The cure schedule was 16 hours at 71° C. and 2 hours at 121° C.

DSC of the cured resin revealed a Tg of 40° C. with a Td of 340° C. TMA determinations gave a Tg of 56° C.

These results indicate that the cured resin formed from the para isomer is more thermally stable and has a higher Tg than the cured resin from the meta isomer of Example 2. This result is expected from the well-established general structure-property relationship of meta and para catenations of polymer chains.

The outgassing results showed a TML of 1.45 % and a CVCM of 0.10%.

EXAMPLE 5

This example illustrates the preparation of α,α'-bis[(3-allylphenyl)dimethylsilyl]-1,4-xylene and α,α'-bis[(3-glycidylphenyl)dimethylsilyl]-1,4-xylene.

The procedure described in Example 1 is followed except that in Step B, Compound (2) is replaced by α,α'-bis(chlorodimethylsilyl)-1,4-xylene and the product formed has the formula:

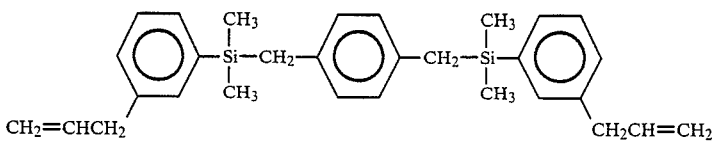

Epoxidation of the above-noted compound as described in Step C of Example 1 produces the product having the formula:

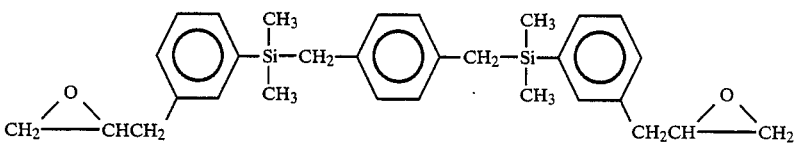

EXAMPLE 6

This example illustrates the preparation of 2,11-bis(3-allylphenyl)-2,11-dimethyl-2,11-disiladodecane [Compound 3, n=4], and 2,11-bis(3-glycidylphenyl)-2,11-dimethyl-2,11-disiladodecane [Compound 4, n=4] in accordance with the present invention.

A. Preparation of 3-(3-bromophenyl)propene:

3-(3-bromophenyl)propene was prepared as described in Example 1, Step A.

B. Preparation of 2,11-bis(3-allylphenyl)-2,11-dimethyl-2,11-disiladodecane:

The compound 2,11-bis(3-allylphenyl)-2,11-dimethyl-2,11-disiladodecane, also named 1,8-bis(3-allylphenyl-dimethylsilyl)octane [Compound 3, where n=4] was prepared in accordance with the reaction shown in Example 1, Step B.

To a flame dried 2-liter 3-neck flask fitted with a reflux condenser and a dropping funnel there was added 13.00 g of magnesium turnings (0.5350 moles) and 200 ml of anhydrous tetrahydrofuran (THF), freshly distilled from sodium. To this mixture was added, via the addition funnel, 10 ml of a solution of 102.27 g (0.5194 moles) of 3-(3-bromophenyl) propene in 200 ml of anhydrous THF.

Following initiation of the reaction, the remainder of the 3-(3-bromophenyl)propene solution was added dropwise at such a rate as to maintain a gentle reflux. After complete addition, the solution was heated at reflux for 1 hour.

A solution of 70.0 g (0.2337 moles) of 2,11-dichloro-2,11-dimethyl-2,11-disiladodecane, available commercially from Petrarch Systems as 1,8-bis(chlorodimethyl-silyl)octane, in 150 ml of anhydrous THF was transferred to the now empty addition funnel and added to the reaction mixture, still under reflux. After complete addition, the reaction was heated at reflux for 1-2 hours, cooled and allowed to stir at room temperature overnight.

Work-up was accomplished by pouring the reaction mixture into 800 ml of a cold, saturated ammonium chloride solution. The aqueous layer was separated and extracted with three 300-ml portions of ether. The combined organic fractions were washed once with aqueous ammonium chloride, once with water, and finally dried over magnesium sulfate.

After the solvents were removed on a rotary evaporation, the crude product was further purified by passing down a Kontes design falling film molecular distillation apparatus at a pressure less than $1 \times 10^{-4}$ torr using refluxing water as the external heating fluid. The yield of the purified product was 86.70 g (80.3%). Characterization data obtained by NMR spectrometry are as follows. $^1$H NMR (CDCl$_3$) δ 0.1 (s, 12H, SiCH$_3$), 0.45 (bm, 4H, SiCH$_2$—), 1.0 (bm, 12H, —CH$_2$—), 3.1 (bd, 4H, benzylic H's), 4.8 (bd, 4H, terminal vinyl H's), 5.7 (bm, 2H, vinyl H), and 7.1 ppm (bm, 8H, aromatic).

C. Preparation of 2,11-bis(3-glycidylphenyl)-2,11-dimethyl-2,11-disiladodecane:

The compound 2,11-bis(3-glycidylphenyl)-2,11-dimethyl-2,11-disiladodecane (Compound 4, where n=4), was prepared in accordance with the reaction shown in Example 1, Step C.

To a 2-liter 3-neck flask equipped with a dropping funnel, mechanical stirrer and reflux condenser was added 85.01 g of 3-chloroperoxybenzoic acid (85% assay) and 450 ml of dichloromethane. The partial solution was heated to reflux, upon which complete solubility was obtained.

To this solution was added at reflux a solution of 86.70 g (0.1877 moles) of 2,11-bis(3-allylphenyl)-2,1-dimethyl-2,11-disiladodecane, Compound 3 where n=4, prepared in Step B above, in 100 ml of dichloromethane. Following complete addition, the reaction mixture was kept at reflux for 15 hours, during which a copious amount of white precipitate formed. The solution was cooled and filtered. The filtrate was concentrated to an oil, resulting in further precipitation. The crude product was filtered, dissolved in 500 ml of hexane, washed with three 100-ml portions of aqueous sodium hydroxide, followed by an aqueous ammonium chloride wash and a final water wash. The hexane solution was dried over magnesium sulfate, filtered, and concentrated.

Final purification of the crude 2,11-bis(3-glycidyl-phenyl)-2,11-dimethyl-2,11-disiladodecane was accomplished by passing it down a Kontes design falling film molecular distillation apparatus at a pressure less than $1 \times 10^{-4}$ torr using refluxing butyl acetate as the external heating fluid. Residual solvent and other volatiles were removed. The final product was characterized by NMR spectrometry as follows. $^1$H NMR (CDCl$_3$) δ 0.1 (s, 12H, SiCH$_3$), 0.45 (bm, 4H, SiCH$_2$), 1.0 (bm, 12H, —CH$_2$—), 2.0-3.9 (overlapping m's, 10H, characteristic of epoxide ring), and 6.8-7.4 ppm (m, 8H, aromatic).

EXAMPLE 7

This example illustrates an alternative method for the preparation of 2,11-bis(3-allylphenyl)-2,11-dimethyl-2,11-disiladodecane (Compound 3, n=4) using an inverse addition mode for the Grignard reaction.

To a flame dried 2-liter 3-neck flask fitted with a mechanical stirrer, reflux condenser, and an addition funnel was added 70.19 g (2.887 moles) magnesium turnings and 500 ml of anhydrous tetrahydrofuran (THF).

A solution consisting of 541.6 g (2.751 moles) of 3-(3-bromophenyl)propene, prepared as in Example 1, Step A, in 150 ml anhydrous THF was placed into the addition funnel. An aliquot of this solution was added to the reaction flask. Reaction initiated immediately and addition was continued dropwise at such a rate as to maintain a gentle reflux. Following complete addition the reaction was heated at reflux for 3 hours.

The addition funnel was replaced with a rubber septum and the reaction mixture transferred via cannulation to a 5-liter flask containing 392.34 g (1.310 moles) of 2,11-dichloro-2,11-dimethyl-2,11-disiladodecane in 1 liter refluxing THF. In a first batch, both flasks were kept at reflux temperature throughout the addition. (In a second batch, both flasks were kept at ambient temperature throughout the addition.) Following complete addition, the reaction was heated an additional half hour at reflux, cooled to room temperature and allowed to stir 16 hours.

Work-up was accomplished by pouring the reaction mixture into 3 liters of cold, saturated aqueous ammonium chloride and extracting with three 750-ml portions of hexane. The combined organic fractions were washed with water and dried over magnesium sulfate. Following solvent removal, final purification was accomplished by passing the crude oil down a falling film molecular distillation apparatus at a pressure less than $10^{-4}$ torr using refluxing water as the heating fluid. The yield was 578.1 g (95.52%) for the first batch and 72.3% for the second batch.

Characterization of the 2,11-bis(3-allylphenyl)-2,11-dimethyl-2,11-disiladodecane reaction product formed by this alternative method was accomplished by spectral comparison with the product of Example 6, Step B.

The above-noted bis-allyl product was epoxidized with 3-chloroperoxybenzoic acid and the epoxy product, Compound 4, n=4, was purified by passage from a falling film molecular distillation apparatus twice at a pressure less than $10^{-4}$ torr using refluxing butyl acetate (125° C.) as the external heating fluid, as described in Example 6, Step C.

A third batch of Compound 3, n=4 was prepared as described above for the first batch, and subsequently epoxidized to produce Compound 4, n=4. Both Compound 3, n=4 and Compound 4, n=4 obtained from this third batch run were fully characterized by the methods and data given below.

For Compound 3, n=4,
$^1$H NMR (250 MHz, CDCl$_3$): δ 0.29 (s, 12H), 0.74–0.81 (bm, 4H), 1.26–1.34 (m, 12H), 3.42 (d, 4H, J=6.6 Hz), 5.08 (bs, 2H), 5.11–5.16 (d, 2H, J=8.9 Hz), 5.93–6.09 (complex m, 2H), and 7.18–7.40 ppm (complex m, 8H).

$^{13}$C NMR (62.8 MHz, CDCl$_3$): δ −2.7, 15.9, 24.1, 29.4, 33.8, 40.5, 115.9, 128.0, 129.2, 131.5, 133.9, 137.7, 139.3, and 140.0 ppm.

Refractive index measured at 24° C.: 1,5223.

IR (film) 2920 (s, sh), 1640 (m,sh), 1410 (s,br), 1250 (s,sh), 1120 (s,sh), 992 (m,sh), 912 (s,br), 865, 835, 810, 780 (s,br), and 710 cm$^{-1}$ (s,br).

Mass Spectrum (22.0 V): m/e 462 (m+, not observed), 344 (36.0), 257 (22.2), and 175 (100.0)

High resolution mass spectrometry gave a molecular ion exact mass measurement of 462.3135 (theoretical: 462.3130).

Analysis. Calculated for C$_{30}$H$_{46}$Si$_2$ (462.870): C, 77.85; H, 10.02; Si, 12.13. Found: C, 77.54; H, 10.31; Si, 12.15.

For Compound 4, n=4
$^1$H NMR (250 MHz, CDCl$_3$); δ 0.26 (s, 12H), 0.71–0.77 (bm, 4H), 1.24–1.29 (bm, 12H), 2.56, 2.57, 2.58, 2.59 (dxd, 2H, J's=5.0, 2.6, Hz), 2.79–2.85 (m, 4H), 2.90, 2.93, 2.96, 2.99 (dxd, 2H, J's=14.4, 5.6 Hz), 3.14–3.20 (bm, 2H), and 7.24–7.41 ppm (complex m, 8H).

$^{13}$C NMR (62.8 MHz, CDCl$_3$): δ −2.8, 15.9, 24.0, 29.4, 33.8, 39.1, 47.0, 52.7, 128.1, 129.6, 132.1, 134.3, 136.5, and 140.3 ppm.

Mass Spectrum (22.0 V): m/e 494 (M+, not observed), 361 (20), 271 (12), 161 (34), 117 (100), and 75 (78).

High resolution mass spectrometry gave a molecular ion exact measurement of 494.3026 (theoretical: 494.3028).

Epoxy equivalent weight:
measured, 267 gm/gm-mole epoxy
theoretical, 247 gm/-mole epoxy

EXAMPLE 8

This example illustrates the characterization of cured resins of 2,11-bis(3-glycidylphenyl)-2,11-dimethyl-2,11-disiladodecane prepared as described in Examples 6 and 7. The viscosity for the uncured epoxy resin prepared as described in Example 7 was 350–356 centipoise. These resins were cured with 1,3-bis(aminopropyl)-1,1,3,3-tetramethyl-1,3-disiloxane (APMD) at the stoichiometries indicated in Table III for 16 hours at 160° F. (71° C.) and post-cured for 4 hours at 250° F. (121° C.). The Tg, Td, and outgassing values measured for the cured resins are shown in Table III. It was noted that the method of Example 7 using inverse addition at reflux resulted in a monomer having a lower epoxy equivalent weight and a cured product having lower outgassing values than the method of Example 7 using inverse addition at ambient temperature.

TABLE III

PROPERTIES OF CURED RESINS (EXAMPLE 8)

| Material | Epoxy Equivalent Weight (eew) | | Stoichiometry (%) | Tg (°C.) | | Td (°C.) | (1) Outgassing (%) | | |
|---|---|---|---|---|---|---|---|---|---|
| | Actual | Theoretical | | TMA | DSC | | TML | CVCM | WVR |
| Example 6 | 321 | 247 | 100 | 3 | −2 | 335 | 0.91 | 0.11 | 0.11 |
| | | | 107 | 20 | 1 | 325 | 1.10 | 0.12 | 0.12 |
| | | | 115 | 37 | 0 | 315 | 1.18 | 0.15 | 0.15 |

TABLE III-continued
PROPERTIES OF CURED RESINS
(EXAMPLE 8)

| Material | Epoxy Equivalent Weight (eew) Actual | Epoxy Equivalent Weight (eew) Theoretical | Stoichiometry (%) | Tg (°C.) TMA | Tg (°C.) DSC | Td (°C.) | Outgassing (%) (1) TML | Outgassing (%) (1) CVCM | Outgassing (%) (1) WVR |
|---|---|---|---|---|---|---|---|---|---|
| Example 7, Batch 2 (Inverse Addition at ambient temperature) | 290 | 247 | 90 | 12 | −4 | 305 | 0.86 | 0.14 | 0.10 |
| | | | 90 | — | — | — | 1.85 | 0.46 | 0.13 |
| | | | 100 | 14 | −2 | 345 | 1.14 | 0.17 | 0.09 |
| | | | 110 | 16 | 5 | 325 | 1.33 | 0.10 | 0.08 |
| Example 7 Batch 1 (Inverse Addition at reflux) | 275 | 247 | 90 | — | — | — | 1.47 | 0.45 | 0.09 |
| | | | 100 | 22 | 5 | 300 | 0.88 | 0.14 | 0.10 |
| | | | 110 | 20 | 8 | 335 | 1.03 (2) | 0.07 | 0.09 |
| Example 7 Batch 3 (Inverse Addition at reflux) | 267 | 247 | 110 | — | 0–15 | 335 | — | — | — |

(1) TML = total mass loss  CVCM = collectable volatile condensable materials  WVR = water vapor recovered
(2) Standard practice allows adjustment of TML values that are slightly greater than 1.0. The adjustment is to subtract the WVR value. The adjusted TML value = 1.03 − 0.09 = 0.94 percent.

EXAMPLE 9

This example illustrates the further characterization of cured resins of 2,11-bis(3-glycidylphenyl)-2,11-dimethyl-2,11-disiladodecane prepared as described in Example 7 and cured with various hardeners. The resin was cured with the hardeners and at the stoichiometries indicated in Table IV. Table IV shows the properties of the cured resins. Table V presents additional mechanical, electrical, and physical properties of the cured epoxy resin formed from the compound prepared as described in Example 7 using 110% stoichiometry of the 1,3-bis(aminobutyl)-1,1,3,3-tetramethyl-1,3-disiloxane (ABMD) hardener (Table IV, item 6).

TABLE IV
PROPERTIES OF RESINS CURED WITH VARIOUS HARDENERS
(EXAMPLE 9)

| Item | Stoichiometry (%) | Hardener | Tg (°C.) TMA | Tg (°C.) DSC | Td (°C.) | Outgassing TML | Outgassing CVCM | Outgassing WVR |
|---|---|---|---|---|---|---|---|---|
| 1 | 90 | APMD | — | −8 | 255 | 1.19 | 0.42 | 0.12 |
| 2 | 100 | APMD | — | 0 | 315 | 0.81 | 0.15 | 0.10 |
| 3 | 110 | APMD | 21 | 2 | 320 | 0.98 | 0.2 | 0.11 |
| 4 | 90 | ABMD | — | −11 | 270 | 1.21 | 0.37 | 0.11 |
| 5 | 100 | ABMD | — | −5 | 320 | 0.95 | 0.30 | 0.12 |
| 6 | 110 | ABMD | 10 | 4 | 310 | 0.98 | 0.08 | 0.11 |
| 7 | 90 | TETA | −16 | — | 210 | — | — | — |
| 8 | 100 | TETA | 20–40 | 15 | 210 | — | — | — |
| 9 | 90 | NMA/2,4EMI | 65 | 43 | 175–177 | — | — | — |
| 10 | 100 | NMA/2,4EMI | 50–74 | 43–52 | 167–188 | — | — | — |

APMD = 1,3-bis(3-aminopropyl)-1,1,3,3-tetramethyl-1,3-disiloxane
ABMD = 1,3-bis(3-aminobutyl)-1,1,3,3-tetramethyl-1,3-disiloxane
TETA = triethylenetetraamine
NMA = nadic methylanhydride, stoichiometry based on anhydride  2,4EMI = 2-ethyl-4-methylimidazole

TABLE V
MECHANICAL, ELECTRICAL, AND PHYSICAL PROPERTIES OF CURED RESIN
(EXAMPLE 9)

| Property | Values |
|---|---|
| Monomer epoxy equivalent weight, g | |
| Actual | 357 |
| Theoretical | 247 |
| Uncured resin viscosity at room temperature, cps | 528 |
| Glass transition temperature, °C. | 4–10 |
| Decomposition temperature, °C. | 310 |
| Outgassing | |
| Total mass loss, % | 0.98 |
| Collectable volatile condensible materials, % | 0.08 |
| Water vapor recovery, % | 0.11 |
| Specific gravity | 1.11 |
| T-peel strength, kg per cm width (lb per in width) | 1.7 (9.4) |
| Elongation, % | 83 |
| Tensile strength, MPa (psi) | 2.3 (330) |
| Lapshear strength, MPa (psi) | 2.7 (400) |
| Dielectric constant at 1 kHz | 3.45 |
| Dissipation Factor at 1 kHz | 0.087 |
| Volume Resistivity, Ω-cm | $4.4 \times 10^{15}$ |
| Dielectric strength, volts/mm (volts/mil) | $4.06 \times 10^5$ ($1.03 \times 10^3$) |

EXAMPLE 10

This example illustrates the preparation of 2,9-bis(3-allylphenyl)-2,9-dimethyl-2,9-disiladecane and 2,9-bis(3-glycidylphenyl)-2,9-dimethyl-2,9-disiladecane.

The procedure (using the normal addition mode) described in Example 6 was followed except that in Step B, Compound 2 where n=4 was replaced with Compound 2 where n=3, and the product formed was Compound 3 where n=3. In Step C, the product formed was Compound 4 where n=3.

The purified product yield for Compound 3 (n=3) was 81.2% and the purified product yield for Compound 4 (n=3) was 80.2%. Compounds 3 and 4 (n=3) were characterized by their respective NMR spectra.

Compound 3 (n=3):

NMR (CDCl$_3$) δ 0.1 (s, 12H, SiCH$_3$), 0.5 (bm, 4H, —SiCH$_2$—), 1.1 (bm, 8H, —CH$_2$—), 3.1 (bd, 4H, benzylic H's), 4.8 (bm, 4H, terminal vinyl H's), 5.35–6.05 (bm, 2H, vinyl H's), and 6.7–7.4 ppm (m, 8H, aromatic).

Compound 4 (n=3):

NMR (CDCl$_3$) δ 0.1 (s, 12H, SiCH$_3$), 0.5 (bm, 4H, —SiCH$_2$—), 1.1 (bm, 8H, —CH$_2$—), 2.1–3.0 (overlapping m's, 10H, characteristic of an epoxide ring), and 6.9–7.4 ppm (m, 8H, aromatic).

The viscosity of Compound 4, n=3 was determined to be 245–250 centipoise.

EXAMPLE 11

This example illustrates an alternative method (the Barbier method) for the preparation of 2,9-bis-(3-allylphenyl)-2,9-dimethyl-2,9-disiladecane (Compound 3, n=3) and 2,9-bis(3-glycidylphenyl)-2,9-dimethyl-2,9-disiladecane (Compound 4, n=3). In the Barbier variation of the Grignard reaction, the organomagnesium reagent is formed in situ in the presence of the electrophile in order to maintain a low concentration of the reagent and thus minimize side reactions. (By contrast in the classic Grignard reaction, the organomagnesium reagent is first formed from R-Br, followed by addition of the electrophile.)

To a flame dried 500 ml 3-neck flask equipped with a magnetic stirrer, reflux condenser, and dropping funnel there was added 9.41 g of dry magnesium (0.3869 moles), 50.00 g of 2,9-dichloro-2,9-dimethyl-2,9-disiladecane (0.1842 moles), and 150 ml anhydrous tetrahydrofuran.

Five ml of a solution of 76.17 g of 3-(3-bromophenyl)-propene, prepared as in Example 1, Step A, (0.3869 moles) in 100 ml anhydrous tetrahydrofuran was added by means of the addition funnel. Reaction initiated immediately and addition of the 3-(3-bromophenyl)propene was continued at a rate to maintain a gentle reflux. Following complete addition, the reaction was heated at reflux for 2 hours, and then cooled to room temperature.

Work-up of the crude product was accomplished by pouring the reaction mixture into 250 ml of a cold, saturated aqueous ammonium chloride solution. The aqueous layer was separated, extracted three times with 100 ml portions of ether. The combined organic fractions were washed once with aqueous ammonium chloride, once with water and dried over magnesium sulfate.

Following solvent removal, the crude oil was purified by passage down a falling film molecular distillation apparatus at a pressure less than $1 \times 10^{-4}$ torr using refluxing butyl acetate as the external heating fluid. The resultant product was identified to be 2,9-bis-(3-allylphenyl)-2,9-dimethyl-2,9-disiladecane by comparing its NMR spectrum with that of the product of Example 10, Compound 3 where n=3.

Epoxidation was accomplished using 3-chloroperoxybenzoic acid to form 2,9-bis(3-glycidylphenyl)-2,9-disilodecane, Compound 4, n=3. To a 2-liter 3-neck flask equipped with a mechanical stirrer, reflux condenser and an addition funnel was added 56.54 g of 3-chloroperoxybenzoic acid (85% assay) and 200 ml of dichloromethane. This solution was heated to reflux and a solution of 55.16 g (0.1271 moles) of 2,9-bis-(3-allylphenyl)-2,9-dimethyl-2,9-disiladecane in 100 ml of dichloromethane was added dropwise. The reaction was kept at reflux for 16 hours during which a copious amount of 3-chlorobenzoic acid precipitated. The reaction was next cooled to room temperature, filtered, and the solids were washed with hexane. The solvents were removed on the rotary evaporator, at which time additional 3-chlorobenzoic acid precipitated. The oil was again filtered, and the precipitate was washed with hexane. The filtrate was washed four times with 5 percent sodium hydroxide, once with saturated aqueous ammonium chloride and once with water. After drying over magnesium sulfate and filtering, the solution was concentrated and the oil was then purified by passage twice down a falling film molecular distillation apparatus at a pressure less than $10^{-4}$ torr using refluxing butyl acetate (125° C.) as the external heating fluid.

The resultant product was identified to be 2,9-bis(3-glycidylphenyl)-2,9-dimethyl-2,9-disiladecane by comparing its NMR spectrum with that of the product of Example 10, Compound 4, n=3.

EXAMPLE 12

This example illustrates the preparation of 2,9-bis(3-allylphenyl)-2,9-dimethyl-2,9-disiladecane, Compound 3, n=3, and subsequent conversion to 2,9-bis(3-glycidylphenyl)-2,9-dimethyl-2,9-disiladecane, Compound 4, n=3. The inverse addition procedure described in Example 7 for batch 1 was followed except that 2,11-dichloro-2,11-dimethyl-2,11-disiladodecane, Compound 2, n=4, was replaced with 2,9-dichloro-2,9-dimethyl-2,9-disiladecane, Compound 2, n=3, which was distilled prior to use. The product at this stage was Compound 3, n=3, whose characterization data are as follows:

$^1$H NMR (250 MHz, CDCl$_3$): δ 0.24 (s, 12H), 0.72 (m, 4H), 1.30 (bs, 8H), 3.36 (d, 4H, J=6.6 Hz), 5.03 (bs, 2H), 5.08 (d, 2H, J=8.1 Hz), 5.88–6.01 (m, 2H), and 7.13–7.35 ppm (Complex m, 8H).

$^{13}$C NMR (62.8 MHz, CDCl$_3$): δ −26, 16.1, 24.1, 33.5, 40.7, 116.0, 128.1, 129.4, 131.7, 134.1, 137.9, 139.4, and 140.1 ppm.

Refractive index measured at 24° C.: 1.5243.

IR (film) 2920 (s,sh), 1640 (m,sh), 1410 (s,br), 1250 (s,sh) 1120 (s,sh), 992 (m,sh), 910 (s,br), 860, 835, 810, 775 (s,br) 710 cm$^{-1}$ (m,sh).

Mass spectrum (22.0 V) m/e 434 (M+, not observed), 316 (59.2), 277 (51.8), 229 (50.0), 198 (41.3), 176 (96.3), 175 (100.0), 140 (25.2), 135 (38.4), 127 (49.1), 126 (74.8), and 98 (21.3).

High resolution mass spectrometry gave a molecular ion exact mass measurement of 434.2809 (theoretical: 434.2817).

The above-noted bis-allyl Compound 3, n=3, was epoxidized in the exact manner as described in Example 7 for Compound 3, n=4. The product after the epoxidation in this case was Compound 4, n=3. Characterization data for Compound 4, n=3 are as follows:

$^1$H NMR (250 MHz, CDCl$_3$): δ 0.26 (s,12H), 0.73 (bm,4H), 1.30 (bs,8H), 2.56, 2.57, 2.58, 2.59, (dxd, 2H, J's=5.0, 2.6 Hz), 2.79, 2.81, 2.83, 2.85 (m, 4H), 2.91, 2.93, 2.96, 2.99 (dxd, 2H, J's=14.4, 5.6 Hz), 3.14–3.20 (bm, 2H), and 7.24–7.41 ppm (complex m, 8H).

$^{13}$C NMR (62.8 MHz, CDCl$_3$): δ —2.9. 15.8, 23.9, 33.3, 39.1, 47.0, 52.6, 128.0, 129.5, 132.0, 134.2, 136.5, and 140.2 ppm.

Mass spectrum (22.0 V): m/e 466 (M+, not observed), 191 (6.3), 175 (4.5), 161 (33.9), 135 (16.6), 117 (58.8), and 75 (100.0).

High resolution mass spectrometry gave a molecular ion exact mass measurement of 466.2693 (theoretical 466.2715).

EXAMPLE 13

This example illustrates the characterization of cured resins of 2.9-bis(3-glycidylphenyl)-2,9-dimethyl-2,9-disiladecane. Using the compounds prepared in Examples 10, 11 and 12, test specimens were prepared at various APMD stoichiometries for thermal and outgass testing. The results are summarized in Table VI. For the epoxy resins from Examples 10 and 11, the epoxy equivalent weights (eew's) were respectively, 18% and 29% higher than and the Tg and Td were comparable to those of the resin from Example 12. However, for the cured resin from the compound of Example 11, the out-gassing was significantly improved (a reduction of 17% and 72% in TML and CVCM, respectively, for the 102% APMD stoichiometry) over that of the cured resin from Example 10 using 100% APMD stoichiometry. These results indicate that in using the synthesis technique of Example 11, the attainment of near-theoretical eew may not be critical for meeting the NASA outgassing requirements ($\leq 1.0\%$ TML and $\leq 0.10$ CVCM).

TABLE VI
PROPERTIES OF CURED RESINS (EXAMPLE 13)

| Material | Monomer Epoxy Equivalent Weight (eew) Actual | Theoretical | Stoichiometry (%) | Tg (°C.) TMA | DSC | Td (°C.) | Outgassing (%) TML | CVCM | WVR |
|---|---|---|---|---|---|---|---|---|---|
| Example 10 | 304 | 233 | 90 | — | — | — | 1.71 | 0.42 | 0.10 |
|  |  |  | 100 | 21 | 0 | 360 | 1.54 | 0.46 | 0.10 |
|  |  |  | 107 | 6 | 6 | 335 | 1.65 | 0.42 | 0.10 |
|  |  |  | 115 | 19 | 4 | 345 | 0.83 | 0.40 | 0.11 |
| Example 11 | 331 | 233 | 91 | —1 | — | 250 | — | — | — |
|  |  |  | 102 | 18 | — | 325 | 1.28 | 0.13 | 0.07 |
|  |  |  | 112 | 16 | — | 325 | 1.44 | 0.16 | 0.07 |
| Example 12 | 258 | 233 | 110 | — | —10 to +18 | 340 | — | — | — |

EXAMPLE 14

This example illustrates the use of 2,5-bis(3-glycidylphenyl)-2,5-dimethyl-2,5-disilahexane, Compound 4, n=1, prepared as described in Example 1, as a flexibilizer for epoxy resins. Sample A was prepared by mixing Compound 4, n=1 with 50% weight Epon 828. Sample B was prepared by mixing Compound 4, n=1 with 50% by weight of a 50:50 mixture of Glyamine 125 and Glyamine 135. The mixtures were cured with APMD for 16 hours at 160° F. (71° C.) and post-cured 4 hours at 250° F. (121° C.). Samples of Epon 828 alone and the Glyamine mixture alone were similarly cured for comparison. The thermomechanical data of the resulting cured resins in shown in Table VII. For Sample A, a 55% increase in T-peel with a decrease in Tg was obtained as compared to Epon 828 alone. For Sample B, a 740% increase in T-peel was obtained with a decrease in Tg as compared to the brittle Glyamine mixture alone. Thus, this compound in accordance with the present invention acts as a flexibilizer. It is expected that the use of the meta isomers of Compound 4, where n=3 or n=4 as flexibilizers in accordance with the present invention will provide further increases in flexibility in the resulting epoxy mixtures as compared to those described above.

TABLE VII
FLEXIBILIZING EFFECTS (EXAMPLE 14)

| Sample | Tg (°C.) DSC | TMA | Td (°C.) | T peel (piw) |
|---|---|---|---|---|
| A | 34 | 43 | 250 | 8.7 |
| Epon 828 | 72 | 93 | 280 | 5.6 |
| B | 27 | 42 | 190 | 4.2 |
| Glyamine Mixture | 45 | 62 | 250 | 0.5 |

Epon 828 is a diglycidyl ether of bisphenol A, from Shell Chemicals
Glyamine mixture comprises 50:50 glyamine 125 and glyamine 135 (diglycidylaniline and diglycidylorthotoluidine, from FIC Resins Division)

EXAMPLE 15

This example illustrates the use of 2,5-bis(4-glycidylphenyl)-2,5-dimethyl-2,5-disilahexane, Compound 4, n=1, prepared as described in Example 3, as a toughener for epoxy resins. Sample A was prepared by mixing Compound 4, n=1, with 50% by weight of a 50:50 mixture of Glyamine 125 and Glyamine 135. Sample B was prepared by mixing Compound 4, n=1, with 70% by weight of a 50:50 mixture of Glyamine 125 and Glyamine 135. The mixtures were cured with APMD for 16 hours at 160° F. (71° C.) and post-cured 4 hours at 250° F. (121° C.). Samples of the Glyamine mixture alone were similarly cured for comparison. The thermomechanical data of the resulting cured resins is shown in Table VIII. For Samples A and B, increases of 65% and 103%, respectively, in T-peel with no significant loss in Tg were obtained. Thus, the para compounds of the present invention act as tougheners. It is expected that the use of para isomers of Compound 4 where n=3 and n=4 as tougheners in accordance with the present invention will provide further increases in toughness in the resulting epoxy mixtures as compared to those described above.

TABLE VIII

| Sample | TOUGHENING EFFECTS (EXAMPLE 15) | | |
|---|---|---|---|
| | Tg (°C.) via DSC | Td (°C.) | T peel (piw) |
| A | 38 | 290 | 1.0 |
| B | 42 | 300 | 1.2 |
| Glyamine mixture | 45 | 295 | 0.6 |

Glyamine mixture - see note to Table VII.

EXAMPLE 16

This example illustrates the characterization of cured resins of the bisallyl compound 2,5-bis(3-allylphenyl)-2,5-dimethyl-2,5-disilahexane, Compound 3, n=1, and 2,11-bis(3-allylphenyl)-2,11-dimethyl-2,11-disiladodecane, Compound 3, n=4, as prepared in Examples 1 and 6, respectively.

The Compound 3, n=1, and Compound 3, n=4 were each cured by hydrosilation as follows. The platinum catalyst was prepared by dissolving 31 mg of chloroplatinic acid into approximately 2 ml of octyl alcohol. The hardener used was PS121 polymethylhydrosiloxane (2–5 centistoke viscosity), obtained from Petrarch Chemicals. Two grams of Compound 3, n=1 were combined with 1.8 g of PS121 and 4 drops of platinum catalyst, and mixed for two minutes. The resulting clear, water-white solution was cured overnight at ambient temperature. The resulting cured specimen was solid, clear, and friable.

Two grams of Compound 3, n=4, were combined with 0.7 g of PS121 and 4 drops of platinum catalyst and mixed for 2 minutes. This gave a cloudy solution which was cured for 1 hour at 100° C., followed by 1 hour at 125° C. The resulting cured specimen was solid, black, and friable.

The DSC results of the cured material obtained from Compound 3, n=1, and Compound 3, n=4, are summarized in Table IX. This data shows that lower Tg's can be obtained from copolymers of the Compound 3 where n=4 than from those of Compound 3 where n=1 with the maintenance of good thermal stability for both species. These results are consistent with those obtained from curing studies performed on Compound 4, n=1, and Compound 4, n=4 as described, respectively, in Example 2 and in Examples 8 and 9.

TABLE IX

| DSC RESULTS OF CURED BISALLYL COMPOUNDS (EXAMPLE 16) | | |
|---|---|---|
| Material | Tg (°C.) | Td (°C.) |
| Compound 3 n = 1 | −50 to −30 | 295 |
| Compound 3 n = 4 | −75 to −50 | 325 |

EXAMPLE 17

This example illustrates the use of 2,11-bis(3-glycidylphenyl)-2,11-dimethyl-2,11-disiladodecene, Compound 4, n=4, as protective coatings for composite structures.

Two 12-ply, 12 inch×12 inch laminates were fabricated using a [90/0/±45/0/90] orientation of unidirectional graphite prepreg of Fiberite 934 (from Fiberite Corp.) on Hysol/Grafil HMS high strength, medium modulus fiber (from Hysol/Grafil Co.). During the prepreg layup, a peel ply was placed on the top ply only. The prepreg layup was press cured as follows: (1) the layup was vacuum bagged and placed in a 250° F. (121° C.) for press for 15 minutes under a minimum vacuum of 27 inches Hg; (2) the bag vacuum was released and 100 psi was applied to the layup for 45 minutes at 250° F. (121° C.); (3) the layup was ramped 2°–6° F./ minute (1°–3° C./minute) to 355° F. (179° C.); (4) the layup was cured for 355° F. (179° C.) for two hours. Immediately prior to coating, the peel ply was removed and half of the front surface of each panel was lightly sanded with 320 grit paper, followed by 500 grit paper. The sanded half of panel A was coated to a dry film thickness of 0.001 inch (0.0254 mm) with Compound 4, n=4, as prepared in Example 7, batch 3 (267 eew), which had been mixed with 100% stoichiometry of triethylenetetraamine. The sanded half of panel B was coated to a dry film thickness of 0.005 inches (0.0127 mm) using Compound 4, n=4, half of which was prepared as in Example 7, batch 3 (267 eew), and half of which was prepared by the process of Example 7 except as modified by the Barbier technique (360 eew). Each batch of resin on panel B was mixed with 100% stoichiometry of triethylenetetraamine and applied as discrete layers. Both panels were cured at 250° F. for three days.

After cure of Compound 4, n=4, the entire surfaces of both panels were immediately coated to a dry film thickness of 0.0006 to 0.0009 inches (0.0152–0.0229 mm) with epoxy primer conforming to MIL-P-23377, Primer Coatings; Epoxy-Polyamide, Chemical and Solvent Resistant. The primed panels were dried one-half hour at ambient temperature, followed by a 2-hour bake at 199° F. (93° C.). The panels were then topcoated to a dry film thickness of 0.0017 to 0.0023 inches (0.0432–0.0584 mm) with polyurethane paint conforming to MIL-C-83286B. Coating, Urethane, Aliphatic Isocyanate, For Aerospace Applications. The panels were cured for seven days at ambient conditions, followed by 96 hours at 210° F. (98.9° C.). Thus, the protected half of each panel comprises a graphite composite laminate, an interlayer of the polymer of the compound of the present invention, a primer layer, and a polyurethane paint layer. The unprotected half of each panel comprises a graphite composite laminate, a primer layer, and a polyurethane paint layer.

Both panels were then subjected to plastic bead blast-,using abrasive blasting machines equipped with Polyextra 20/30 Type AGO plastic bead media, manufactured by U.S. Plastics and Chemical Co. The blast nozzle pressure was 70 psi (0.5 megapascals). The pellet blasts were directed at the center of each panel to simultaneously remove the paint on the unprotected half of the panel and on the half of the panel protected with the polymer of Compound 4, n=4 as an interlayer.

For Panel A, it was found that the interlayer of the polymer of Compound 4, n=4 was still intact after complete paint and primer removal from a 2.18 inch (55.4 mm) area. By contrast, one ply of the graphite composite material on the unprotected side in a 2.25 inch (57.2 mm) area had been penetrated, leaving several depressions, the largest of which was 0.252 inches (6.4 mm) long by 0.30 inches (7.6 mm) wide. When pellet blasting was repeated in a fresh area for sufficient time to damage the interlayer of the polymer of Compound 4, n=4, the majority of the interlayer was intact, with one ply of graphite composite material being removed in four places in the 1.655 inch (42.0 mm) long area. The largest depression on the interlayer was found to be 0.20 inch (5.1 mm) long by 0.15 inch (3.8 mm)

composite material had been removed throughout the bulk of the 1.2 inch (30.5 mm) long blasted area.

For panel B, it was found that the interlayer of the polymer of Compound 4, n=4 was still intact after complete paint and primer removal of a 1.5 inch (38.1 mm) long area, while extensive damage (removal of 5–12 plies of the composite) to the unprotected side resulted. In particular, a 0.237 inch (6.2 mm) by 0.373 inch (9.5 mm) hole through the composite was made by the pellet blasting within a 1.684 inch (42.8 mm) long area. When the pellet blasting was repeated for a sufficient time to damage the interlayer of the polymer of Compound 4, n=4, in a fresh area, the bulk of the 1.47 inch (37.4 mm) long area still had intact its coating of the polymer of Compound 4, n=4, with a depression of 0.418 inches (10.6 mm) by 0.322 inch (8.2 mm) at the center of the panel, where 2–3 plies of composite had been removed. On the unprotected side, extensive damage (removal of 5 to 12 plies of composite) resulted. In particular, 0.388–0.486 inch (9.9–12.3 mm) long by 0.934 inch (23.7 mm) wide hole through the composite was made by the pellet blast.

This testing illustrates the excellent abrasion damage resistance of a layer of the polymer of Compound 4, n=4. Polymers of other compounds in accordance with the present invention are expected to exhibit similar abrasion resistance. It is expected that coatings of polymers of this compound and its analogs will also exhibit good resistance to damage by plasma particles due to their unique chemical and physical characteristics. Possible uses of these coatings in accordance with the present invention include that of a plasma mask and as abrasion resistant coatings or masks for aircraft and spacecraft applications. In addition, copolymers in accordance with the present invention which exhibit appropriate toughness are also expected to exhibit good resistance to mechanical or plasma abrasion.

As can be seen from the data presented in the Examples herein, the compounds of the present invention provide resins which possess thermal stability, toughness, and low outgassing properties. By selection of the appropriate isomeric structure and chain length of the compounds of the present invention and selection of the appropriate hardener for curing these compounds, the rigidity of the resulting structure may be tailored anywhere within the range from soft rubbers to hard, tough plastics. These properties make the compounds of the present invention especially useful for forming improved encapsulants, primers, topcoats, and adhesives for a variety of substrate materials, such as aluminum and graphite-epoxy composites. In particular, due to the low outgassing properties, the compounds of the present invention are well suited for use in space applications. In addition, the epoxy monomer compounds of the present invention may be copolymerized with known epoxy resin coatings, adhesives, and encapsulants to toughen or to flexibilize them. Moreover, the ethenyl monomers of the present invention are useful for forming polymers and copolymers for applications as low dielectric materials. Finally, the polymers and copolymers of the present invention are useful as abrasion-resistant coatings.

Having thus described exemplary embodiments of the present invention, it should be noted by those skilled in the art that the disclosures within are examplary only and that various other alternatives, adaptations and modifications may be made within the scope of the present invention. Accordingly, the present invention is not limited to the specific embodiments as illustrated herein, but is only limited by the following claims.

What is claimed is:

1. A polymer material formed by polymerization of a compound having the formula

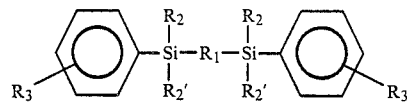

where $R_1$ is selected from the group consisting of
   (a) an aliphatic hydrocarbon group containing 2 to 10 carbon atoms, and
   (b) a group having the formula

where
   n=1 to 3
   m=0 to 5;

$R_2$ and $R_2'$ are each selected from the group consisting of an alkyl group containing 1 to 4 carbon atoms, an unsubstituted aryl group, and a substituted aryl group; and $R_3$ is selected from the group consisting of:

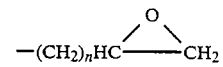

and

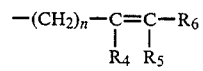

where $R_4$, $R_5$, and $R_6$ are each selected from the group consisting of H, an alkyl group containing 1 to 4 carbon atoms, and an aryl group; and n=0 to 10.

2. A copolymer formed by polymerizing:
   (1) a first monomer compound of the formula I:

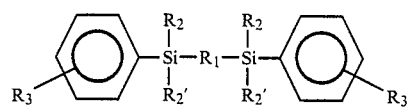

where $R_1$ is selected from the group consisting of:
   (a) an aliphatic hydrocarbon group containing 2 to 10 carbon atoms, and
   (b) a group having the formula

where
   n=1 to 3
   m=0 to 5;

$R_2$ and $R_2'$ are each selected from the group consisting of an alkyl group containing 1 to 4 carbon atoms, an unsubstituted aryl group, and a substituted aryl group; and $R_3$ is selected from the group consisting of:

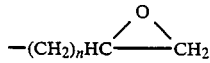

and

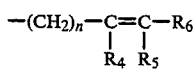

where $R_4$, $R_5$, and $R_6$ are each selected from the group consisting of H, an alkyl group containing 1 to 4 carbon atoms, and an aryl group; and n=0 to 10, and (2) a second chosen monomer capable of copolymerization compound of Formula I to form said copolymer.

3. A copolymer according to claim 2 wherein $R_3$ comprises

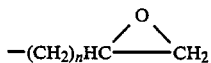

where
n=0 to 10, and
said second monomer is selected from the group consisting of a compound having an epoxy group and a compound having a siloxane group.

4. A copolymer according to claim 2 wherein said compound of Formula I comprises 10 to 90 percent by weight of the mixture from which said copolymer is formed.

5. An article comprising a chosen substrate having formed on the surface thereof a layer of the cured polymer set forth in claim 1.

6. An article comprising a chosen substrate having formed on the surface thereof a layer of the cured copolymer set forth.

7. A copolymer as set forth in claim 3 comprising:
 (a) a predetermined amount within the range of 90 to 20 percent by weight of said epoxy compound; and
 (b) a predetermined amount within the range of 10 to 80 percent by weight of said compound of formula I where R3 is attached to the phenylene group in the meta position, wherein said copolymer has increased flexibility compared to the polymerized product of said epoxy compound alone.

8. A copolymer according to claim 7 wherein said predetermined amount of said compound of formula I comprises about 30 to 50 percent by weight.

9. A copolymer as set forth in claim 3 comprising:
 (a) a predetermined amount within the range of 90 to 20 percent by weight of said epoxy compound; and
 (b) a predetermined amount within the range of 10 to 80 percent by weight of said compound of formula I where R3 is attached to the phenylene group in the para position, wherein said copolymer has increased toughness compared to the polymerized product of said epoxy compound alone.

10. A copolymer according to claim 9 wherein said predetermined amount of said compound of formula I comprises about 30 to 50 percent by weight.

* * * * *

UNITED STATES PATENT AND TRADEMARK OFFICE
CERTIFICATE OF CORRECTION

PATENT NO. : 4,916,038

DATED : April 10, 1990

INVENTOR(S) : KREISLER S.Y. LAU, SUSAN L. OLDHAM, WILLIAM E. ELIAS and STEPHEN J. BIGUS It is certified that error appears in the above-identified patent and that said Letters Patent is hereby corrected as shown below:

Col. 2, line 67, delete "2" and insert therefor --1--.

Col. 3, line 42, after "ω", insert --a hyphen (-)--.

Col. 8, line 32, after "3", insert --a hyphen (-)--.

Col. 11, line 3, delete "⊕" and insert therefor --δ--.

Col. 14, line 10, after "dimethyl", delete parenthesis ( )).

Col. 16, line 44, delete "2,1-" and insert therefor --2,11- --.

Col. 29, line 18, after "ization", insert --with said--.

Col. 30, line 8, after "forth", add --in claim 2.--.

Signed and Sealed this

Eighth Day of October, 1991

Attest:

HARRY F. MANBECK, JR.

*Attesting Officer*   *Commissioner of Patents and Trademarks*